United States Patent [19]

Whiting

[11] Patent Number: 5,171,591
[45] Date of Patent: Dec. 15, 1992

[54] CONTROL OR ELIMINATION OF UNDESIRABLE BACTERIA USING PARASITIC BDELLOVIBRIO BACTERIA

[75] Inventor: Richard C. Whiting, Ambler, Pa.

[73] Assignee: The United States of America as represented by the Secretary of Agriculture, Washington, D.C.

[21] Appl. No.: 694,602

[22] Filed: May 2, 1991

Related U.S. Application Data

[63] Continuation-in-part of Ser. No. 518,676, May 3, 1990, abandoned.

[51] Int. Cl.$^5$ .................................. A23B 4/14
[52] U.S. Cl. .......................... 426/43; 426/56; 426/320; 426/335; 134/25.2; 134/25.3
[58] Field of Search .................. 426/61, 321, 7, 42, 426/43, 52, 56, 320, 335; 134/25.2, 25.3

[56] References Cited

U.S. PATENT DOCUMENTS

| | | |
|---|---|---|
| 3,457,086 | 7/1969 | Josefowicz. |
| 4,425,370 | 1/1984 | Graves. |
| 4,666,842 | 5/1987 | Uwajima ............... 435/189 |
| 4,810,385 | 3/1989 | Hater ..................... 210/632 |

FOREIGN PATENT DOCUMENTS

| | | |
|---|---|---|
| 0151450 | 8/1985 | European Pat. Off. . |
| 0203628 | 3/1986 | European Pat. Off. . |
| 0157954 | 4/1987 | European Pat. Off. . |
| 0253429 | 1/1988 | European Pat. Off. . |
| 0279498 | 8/1988 | European Pat. Off. . |
| 0279499 | 8/1988 | European Pat. Off. . |
| 0304131 | 2/1989 | European Pat. Off. . |
| 0297690 | 4/1989 | European Pat. Off. . |
| 2302103 | 9/1976 | Fed. Rep. of Germany . |
| 1113241 | 5/1968 | United Kingdom . |

OTHER PUBLICATIONS

Neal 1977 J. Food Science 42(2) 555.
Burnham 1984 Bergey's Manual of Systematic Bactereology pp. 118-124.

*Primary Examiner*—Carolyn Paden
*Attorney, Agent, or Firm*—M. Howard Silverstein; John D. Fado; Joseph A. Lipovsky

[57] ABSTRACT

Parasitic bacteria of the genus Bdellovibrio are utilized to control or eliminate undesirable bacteria in or on: certain foods for human consumption; or a food contact surface(s) (i.e. the Bdellovibrio attack and kill undesirable bacteria indigenous to the food or food contact surface(s)). A wide variety of pathogenic (e.g. Salmonella, Vibrio, Shigella, Escherichia, Campylobacter and Yersinia), and food spoilage bacteria (e.g. Pseudomonas, Aeromonas and Enterobacteriaceae) may be controlled or eliminated by parasitization by the Bdellovibrio bacteria.

15 Claims, No Drawings

CONTROL OR ELIMINATION OF UNDESIRABLE BACTERIA USING PARASITIC BDELLOVIBRIO BACTERIA

CROSS-REFERENCE TO RELATED APPLICATION

The present application is a continuation-in-part of application Ser. No. 07/518,676 filed May 3, 1990, entitled "Reduction of Undesirable Bacteria Using Parasitic Bdellovibrio Bacteria" by Richard C. Whiting, now abandoned.

FIELD OF THE INVENTION

The instant invention is drawn to use of viable bacteria of the genus Bdellovibrio to control or eliminate undesirable bacteria in or on: food contact surfaces (i.e. this does not encompass the surface of a food); or certain foods for human consumption.

BACKGROUND

Foods and food contact surfaces are susceptible to contamination by undesirable bacteria (e.g. food-borne pathogenic or food spoilage bacteria). For example, Salmonella (the most important cause of food-borne disease outbreaks in the United States) is estimated to be responsible for over a billion dollars annually of losses to the U.S. economy. However, extensive research over many years has been unsuccessful in eliminating this problem, indicating the need for entirely new approaches to this long-standing problem. The present invention is directed to a unique, totally new approach to this restive problem area, through the application of the principles of biological control of the microbiological environment.

The few attempts at biological control in food-associated microbiological ecologies have for the most part used competitive species or their active products, such as lactic acid bacteria and nisin, respectively. However, control in these instances is limited by its passivity, whereas by contrast, the present invention employs an active process involving aggressive predators of pathogenic bacteria.

Neal et al in "Bdellovibrio in Foods" Journal of Food Science, Vol. 42, No.2 (1977), pages 555-556, disclose inoculating ground beef and fluid milk with Bdellovibrio, but discuss only spoilage microorganisms, provide meager data and achieve only negative results. By contrast the present invention is directed to reduction of both pathogenic and spoilage bacteria, and specifically excludes the treatment of ground beef and fluid milk.

An English language abstract of French patent 2,302,103 issued Oct. 29, 1976 to M. Plisser, refers to using Bdellovibrio as an additive for animal feeds. By contrast the present invention is directed to certain foods for human consumption.

SUMMARY OF THE INVENTION

The present invention relates to utilization of viable bacteria of the genus Bdellovibrio to control or eliminate undesirable bacteria in/on: one or more food contact surface(s) other than a surface of a food (i.e. surface(s) which are contacted with food, e.g. surfaces in or on food storage or processing equipment or tools, food processing facilities, and food work surfaces); or a food for human consumption selected from the group consisting of fish, shellfish, poultry, eggs, a milk product other than fluid milk, pork, lamb, veal and beef which has not been ground. Further the present invention encompasses: placing in contact with (e.g. inoculating into and/or applying onto) the aforementioned foods for human consumption, or onto food contact surfaces; viable bacteria of the genus Bdellovibrio in a concentration sufficient to control or eliminate said undesirable bacteria. These bacteria then attack and kill indigenous undesirable bacteria.

*Bdellovibrio bacteriovorous* is a gram-negative, aerobic parasite of Salmonella and other gram-negative bacteria of both public health and food spoilage concern; and therefore provides a means of controlling a variety of important food-borne disease-causing bacteria, and may be utilized to extend the shelf-life of important agricultural products.

Other objects and advantages of the present invention will become readily apparent from the ensuing description.

DESCRIPTION OF THE PREFERRED EMBODIMENTS

Bdellovibrio are comma-shaped, motile rods with a two-stage life cycle that encompasses a non-growing predatory phase followed by a reproductive phase within the host (for greater detail see *Bergy's Manual of Systematic Bacteriology,* 1984, pages 118-124, "Genus Bdellovibrio"). No strains have been isolated that invade gram-positive bacteria or eucaryotic cells. Bdellovibrio are found naturally in soil, sewage, fresh water and marine environments. All strains isolated from natural sources are obligate parasites, though some clones have been developed that can be propagated in complex culture media.

The Bdellovibrio may be inoculated into the food or applied to the food or food contact surface in a suspension which also includes millimolar concentrations of calcium and magnesium, at or near a neutral pH. Bdellovibrio require oxygen for their activity. They have increasing activity with increasing temperature, to a maximum at approximately 35°-40° C. Bdellovibrio may be stored as the free-swimming stage or as partially grown inside the prey bacteria. Storage may be as either frozen or freeze dried cells.

In accordance with the present invention viable bacteria of the genus Bdellovibrio may be utilized to control or eliminate undesirable bacteria including: (1) pathogenic bacteria, such as, Salmonella, Vibrio, Shigella, Escherichia, Campylobacter, and Yersinia: and (2) food spoilage bacteria, such as, Pseudomonas, Aeromonas and Enterobacteriaceae.

The present invention may be practiced with any of the aforementioned foods for human consumption as these foods are susceptible to infestation by undesirable bacteria, and the instant invention increases the shelf life of such foods and reduces detrimental effects (if any) of consuming the undesirable bacteria (if any) thereon. Specifically, said foods for human consumption include: fish, shellfish (e.g. shrimp, clams, etc.), poultry (such as chicken, turkey, duck, goose, quail, pheasant, etc.), eggs (including eggs of any of the aforementioned poultry), a milk product other than fluid milk (e.g. cheese, yogurt, dried milk, etc.), pork, lamb, veal and beef which has not been ground.

Food contact surfaces which may be treated in accordance with the present invention include: (1) surfaces in food storage or processing equipment (e.g. refrigerators, freezers, grinders, trimmers, slicers, tenderizers, packing equipment, food transporting equipment, etc.); (2) surfaces in/on tools (e.g. knives, forks, protective equipment, etc.); (3) surfaces (e.g. walls, floors, ceilings, shelves, etc.) in food processing facilities; and, (4) food work surfaces (e.g. cutting blocks, counters, trays, holders, etc.). The phrase "food contact surface" is used herein in conformance with its usual and conventional art accepted meaning, to refer to surfaces such as those delineated hereinabove, and therefore said phrase does not encompass a surface of a food.

In accordance with the present invention the Bdellovibrio may be applied in a concentration of on the order of $10^6$ per milliliter, to produce a concentration on the food or food contact surface of from about $10^3$ to about $10^5$ bacteria per square centimeter.

Attack of undesirable bacteria by Bdellovibrio may be enhanced by use of warm temperatures (e.g. 20° C. to 35° C.) and the presence of oxygen. Trace amounts of calcium and magnesium may be added.

Use of Bdellovibrio may be integrated into various points in industrial processes, such as: (1) precooked meat and shellfish products which are sprayed with Bdellovibrio containing solution immediately after cooking and before packaging; (2) purging of shellfish; (3) sanitizing food equipment and facilities; and, (4) during fermentation of dairy products.

The Bdellovibrio may be applied using various methods including: spraying, injecting, brushing, rubbing (as for example with a disposable wipe), or use of a applicator (e.g. roller), or; by dipping, submerging or rolling the food or food contact surface in the Bdellovibrio, or; by mixing the food with the Bdellovibrio, or; by incorporating the Bdellovibrio into, or placing the Bdellovibrio onto, a container or wrapper into/onto which the food or food contact surface is placed or contained. Thus, the present invention encompasses: (1) applying the Bdellovibrio onto an exterior surface of the food; or (2) injecting the Bdellovibrio into the food; or (3) both injecting the Bdellovibrio into the food and applying the Bdellovibrio onto an exterior surface of the food.

The foregoing detailed description is given merely for purposes of illustration. Modifications and variations may be made therein without departing from the spirit and scope of the invention which is defined by the appended claims.

I claim:

1. A manufacture comprising:
a food for human consumption selected from the group consisting of fish, shellfish, poultry, eggs, a milk product other than fluid milk, pork, lamb, veal and beef which has not been ground;
in contact with bacteria of the genus Bdellovibrio in a concentration sufficient to control or eliminate undesirable bacteria.

2. The manufacture of claim 1 wherein said bacteria of the genus Bdellovibrio are present in a concentration of from about $10^3$ to about $10^5$ bacteria per square centimeter.

3. The manufacture of claim 1 comprising said food having bacteria of the genus Bdellovibrio therein.

4. The manufacture of claim 1 comprising said food having bacteria of the genus Bdellovibrio thereon.

5. The manufacture of claim 4 comprising said food having bacteria of the genus Bdellovibrio thereon and therein.

6. The manufacture of claim 1 wherein said poultry is selected from the group consisting of: chicken, turkey, duck, goose, quail and pheasant.

7. The manufacture of claim 1 wherein said milk product other than fluid milk is selected from the group consisting of: cheese, yogurt and dried milk.

8. A process of controlling or eliminating undesirable bacteria in or on: food for human consumption selected from the group consisting of fish, shellfish, poultry, eggs, a milk product other than fluid milk, pork, lamb, veal and beef which has not been ground, comprising: placing in contact with said food, bacteria of the genus Bdellovibrio in a concentration sufficient to control or eliminate said undesirable bacteria.

9. The process of claim 8 wherein said Bdellovibrio are applied in a concentration of from about $10^3$ to about $10^5$ bacteria per square centimeter.

10. The process of claim 8 wherein said step of placing includes applying said Bdellovibrio onto an exterior surface of said food.

11. The process of claim 8 wherein said step of placing includes spraying said Bdellovibrio onto said food or food contact surface.

12. The process of claim 8 wherein said step of placing includes injecting said Bdellovibrio into said food.

13. The process of claim 8 wherein said step of placing includes both, injecting said Bdellovibrio into said food and applying said Bdellovibrio onto an exterior surface of said food.

14. The process of claim 8 wherein said poultry is selected from the group consisting of: chicken, turkey, duck, goose, quail and pheasant.

15. The process of claim 8 wherein said milk product other than fluid milk is selected from the group consisting of: cheese, yogurt and dried milk.

* * * * *